United States Patent
Traber

(10) Patent No.: US 9,339,515 B2
(45) Date of Patent: *May 17, 2016

(54) METHOD FOR TREATMENT OF PULMONARY FIBROSIS

(71) Applicant: Galectin Therapeutics, Inc., Norcross, GA (US)

(72) Inventor: Peter G. Traber, Norcross, GA (US)

(73) Assignee: Galectin Therapeutics, Inc., Norcross, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/999,389

(22) Filed: Feb. 20, 2014

(65) Prior Publication Data

US 2014/0235571 A1   Aug. 21, 2014

Related U.S. Application Data

(60) Provisional application No. 61/767,057, filed on Feb. 20, 2013.

(51) Int. Cl.
A61K 31/736 (2006.01)
A61K 31/715 (2006.01)

(52) U.S. Cl.
CPC ............. *A61K 31/736* (2013.01); *A61K 31/715* (2013.01)

(58) Field of Classification Search
None
See application file for complete search history.

(56) References Cited

U.S. PATENT DOCUMENTS

| | | | |
|---|---|---|---|
| 2,132,577 A | 10/1938 | Olsen et al. | |
| 2,444,266 A | 6/1948 | Maclay et al. | |
| 2,503,258 A | 4/1950 | Graham et al. | |
| 4,016,351 A | 4/1977 | Eschinasi et al. | |
| 4,268,533 A | 5/1981 | Williams et al. | |
| 4,686,106 A | 8/1987 | Ehrlich et al. | |
| 5,071,970 A | 12/1991 | le Grand et al. | |
| 5,498,702 A | 3/1996 | Mitchell et al. | |
| 5,652,109 A | 7/1997 | Kim et al. | |
| 5,681,923 A | 10/1997 | Platt | |
| 5,834,442 A | 11/1998 | Raz et al. | |
| 5,895,784 A | 4/1999 | Raz et al. | |
| 6,329,422 B1 | 12/2001 | Fischer et al. | |
| 6,413,494 B1 | 7/2002 | Lee | |
| 6,417,173 B1 | 7/2002 | Roufa et al. | |
| 6,423,314 B2 | 7/2002 | Platt et al. | |
| 6,500,807 B1 | 12/2002 | Platt et al. | |
| 6,573,245 B1 | 6/2003 | Marciani | |
| 6,632,797 B2 | 10/2003 | Siren | |
| 6,642,205 B2 | 11/2003 | Klyosov | |
| 6,645,946 B1 | 11/2003 | Klyosov | |
| 6,652,856 B2 | 11/2003 | Gotwals et al. | |
| 6,680,306 B2 | 1/2004 | Chang et al. | |
| 6,756,362 B2 | 6/2004 | Roufa et al. | |
| 6,770,622 B2 | 8/2004 | Jarvis et al. | |
| 6,787,521 B2 | 9/2004 | Culler et al. | |
| 6,812,230 B2 | 11/2004 | Horuk | |
| 6,844,354 B1 | 1/2005 | Iizuka et al. | |
| 6,890,906 B2 | 5/2005 | Chang et al. | |
| 6,893,637 B1 | 5/2005 | Gilbertson | |
| 6,914,055 B2 | 7/2005 | Klyosov | |
| 6,936,618 B2 | 8/2005 | Dormer et al. | |
| 6,964,761 B1 | 11/2005 | Condos et al. | |
| 6,982,255 B2 | 1/2006 | Klyosov | |
| 6,986,995 B2 | 1/2006 | Rose et al. | |
| 7,012,068 B2 | 3/2006 | Klyosov | |
| 7,078,064 B2 | 7/2006 | Zabrecky | |
| 7,491,708 B1 | 2/2009 | Platt | |
| 7,893,252 B2 | 2/2011 | Platt | |
| 8,128,966 B2 | 3/2012 | Staples et al. | |
| 8,187,642 B1 | 5/2012 | Staples | |
| 8,236,780 B2 | 8/2012 | Platt et al. | |
| 8,409,635 B2 | 4/2013 | Staples et al. | |
| 8,420,133 B2 | 4/2013 | Staples et al. | |
| 8,722,645 B2 | 5/2014 | Platt et al. | |
| 2003/0004132 A1 | 1/2003 | Chang et al. | |
| 2003/0013682 A1 | 1/2003 | Banito et al. | |
| 2004/0023925 A1 | 2/2004 | Chang et al. | |
| 2004/0043962 A1 | 3/2004 | Chang et al. | |
| 2004/0121981 A1 | 6/2004 | Chang et al. | |
| 2004/0223971 A1 | 11/2004 | Chang et al. | |
| 2005/0008572 A1 | 1/2005 | Prokop et al. | |
| 2005/0250735 A1 | 11/2005 | Staples et al. | |
| 2006/0024357 A1 | 2/2006 | Carpenter et al. | |
| 2006/0067927 A1 | 3/2006 | Chandrasekaran et al. | |
| 2006/0074050 A1 | 4/2006 | Chang et al. | |
| 2006/0094688 A1 | 5/2006 | Tanaka et al. | |
| 2006/0211653 A1 | 9/2006 | Ni et al. | |
| 2008/0089959 A1 | 4/2008 | Chang et al. | |
| 2008/0107622 A1 | 5/2008 | Platt et al. | |

(Continued)

FOREIGN PATENT DOCUMENTS

RU   2240123   11/2004
WO   85/05031 A1   11/1985

(Continued)

OTHER PUBLICATIONS

Banh et al. "Tumor galectin-1 mediates tumor grmvih and metastasis through regulation of T-cell apoptosis ," Cancer Res. 71:4423-31 (2011).
Barondes et al., "Galectins: a family of animal beta-galactoside-binding lectins [letter]," Cell. (76):597-598 (1994).
Barrow at al,, "The role of galectins in colorectal cancer proaression," Int. J. Cancer. 129:1-8(2011b).
Cay et al., "Review Immunohistochemical expression of galectin-3 in cancer: a review of the literature," Patoki Derg. 28(1): 1-10 (2012).
Forsman et al., "Galectin 3 aggrevates joint inflammation and destruction in antigen-induced arthritis," Arthritis Reum. 63: 445-454 (2011).
Godwin, "Histochemical Uses of Haematoxylln—A Review," JPCS. 1: 24-34 (2011).

(Continued)

*Primary Examiner* — Layla Berry
(74) *Attorney, Agent, or Firm* — Greenberg Traurig, LLP

(57) ABSTRACT

Methods and compositions of the invention relate to the treatment of pulmonary fibrosis.

10 Claims, 16 Drawing Sheets
(16 of 16 Drawing Sheet(s) Filed in Color)

(56) References Cited

U.S. PATENT DOCUMENTS

| | | |
|---|---|---|
| 2011/0046086 A1 | 2/2011 | Yun et al. |
| 2011/0077217 A1 | 3/2011 | Platt et al. |
| 2012/0282220 A1 | 11/2012 | Platt et al. |
| 2013/0261078 A1 | 10/2013 | Zomer et al. |

FOREIGN PATENT DOCUMENTS

| | | |
|---|---|---|
| WO | 2004/091634 A1 | 10/2004 |
| WO | 2005/020900 | 3/2005 |
| WO | 2005/025501 | 3/2005 |
| WO | 2005/037293 | 4/2005 |
| WO | 2005/095463 | 10/2005 |
| WO | 2012/162531 A1 | 11/2012 |
| WO | 2013/184892 A1 | 12/2013 |

OTHER PUBLICATIONS

Kolatsi-Joannou et al., "Modified citrus pectin reduces galectin-3 expression and disease severity in experimental acute kidney injury," PLoS One. 6: el8683, doi:l0.1371/journal.pone.0018683 (2011).

Lefranc et al., "Galectin-1 mediated biochemical controls of melanoma and glioma aggressive behavior," World J. Biol. Chem. 2: 193-201 (2011).

Liu et al., "Galectins in regulation of inflanmmtion and immunity," In Galectins (ed. By Klyosov, A.A., Witzhak, Z.A., and Platt, D.), John Wiley & Sons, Hoboken, New Jersey, pp, 97-113 (2008)

Lopez et al., "Gene expression profiling in lungs of chronic asthmatic mice treated with galectin-3: downregulation of inflammatory and regulatory genes," Mediators Inflamm.,823279. Epub Mar. 20, 2011.

Newlaczyl et al., "Galectin-3—a jack-of-all-trades in cancer," Cancer Lett. 313: 123-128 (2011).

Ohshima et al., "Galectin 3 and its binding protein in rheumatoid arthritis," Arthritis Rheum. 48: 2788-2795 (2003)

Sato et al., "Galectins as danger signals in host-pathogen and host-tumor interactions: new members of the growing group of Alarmins." In "Galectins," (Klyosov, et al eds.), John Wiley and Sons, 115-145 (20080.

Toussaint et al., "Galectin-1, a gene preferentially expressed at the tumor margin, promotes glioblastoma cell invasion", Mol Cancer. 11: 32. (2012).

Wang et al., "Nuclear and cytoplasmic localization of galectin-1 and galectin-3 and their roles in pre-mRNA splicing." In "Galectins" (Klyosov et al eds.), John Wiley and Sons, 87-95 (2008).

International Search Report and Written Opinion from International Application No. PCT/US2012/055311 dated Nov. 21, 2012.

International Search Report and Written Opinion from International Application No. PCT/US2014/017353 dated May 12, 2014.

MacKinnon et al., "Regulation of Transforming Growth Factor-Beta1-driven Lung Fibrosis by Galectin-3", American Journal of Respiratory and Critical Care Medicine, vol. 185, Iss. 5, pp. 537-546. Mar. 1, 2012.

Gura, "Systems for Identifying New Drugs Are Often Faulty", www.sciencemag.org, Science, vol. 278, Nov. 7, 1997, pp. 1041-1042.

Bataller et al. "Liver Fibrosis" The Journal of Clinical Investigation, 2005, vol. 115, No. 2, pp. 209-218.

Desmouliere et al. "Tissue Repair, Contraction, and the Myofibroblast," Wound Repair and Regeneration. 13(1): 7-12 (2005).

Fitzner et al. "Galectin-1 is an inductor of pancreatic stellate cell activation" Cellular Signaling, 2005, 17: 1240-1247.

Friedman Hepatic Fibrosis: Chapter 10, "Diseases of the Liver," Schiff, Sorrell and Maddrey eds. 8th Edition, 1999.

Friedman "Liver Fibrosis—From Bench to Bedside," Journal of Hepatology. 38: S38 (2003).

Friedman "Mechanisms of Disease: Mechanisms of Hepatic Fibrosis and Therapeutic Implications," Nature Clinical Practice: Gastroenterology & Hepatology 1(2): 98 (2004).

Friedman "Molecular Regulation of Hepatic Fibrosis, an Integrated CellularResponse to Tissue Injury," Journal of Biological Chemisty. 275: 2247 (2000).

Hetzel et al. "Different Effects of Growth Factors on proliferation and Matrix Production of Normal and Fibrotic Human Lung Fibrobalsts", 2005, Lung, 225-237.

Gillissen et al. "Characterization of N-Acetylcysteine and Ambroxol in Anti-Oxidant Therapy," Respiratory Medicine, 92: 609-623 (1998).

Kasper et al. "Immunocytochemical Evidence for a Modulation of Galectin 3 (Mac-2), a Carbohydrate Binding Protein, in Pulmonary Fibrosis," Journal of Pathology 179(3):309-319 (1996).

Lopez et al. "Inhibition of Chronic Airway Inflammation and Remodeling by Galectin-3 Gene Therapy in a Murine Model," Journal of Immunology, Feb. 1, 2006;176(3):1943-50.

Maeda et al, "Stimulation of Proliferation of Rat Hepatic Stellate Cells by Galectin-1 and Galectin-3 through different Intracellular Signaling Pathways", Journal of Biol. Chem. 2003, vol. 278, No. 21, pp. 18938-18944.

The Merck Manual of Diagnosis and Therapy (17th edition), 1999, Published by Merck Research Laboratories, pp. 372-374 (1999).

The Merck Manual of Diagnosis and Therapy (19th edition), 2011, Chapter 3: Hepatic and Bilary Disorders, pp. 205-280, Published by Merck Sharp & Dohme Corp., Whitehouse Station, NJ.

di Mola et al. "Connective Tissue Growth Factor is a Regulator for Fibrosis in Human Chronic Pancreatitis," Annals of Surgert, 230(1): 63 (1999).

Nergard et al., "Structural and Immunological Studies of a Pectic Arabinogalactan from Vernonia Kotschyana Sch. Bip. Ex. Wap. (Asteraceae)," Carbohydrate Research. 340:115-130 (2005).

Ouchi T et al. "Synthesis and Cytotoxic Activity of Oxidized Galactomannan/ADR Conjugate" Journal of Macromolecular Science, Part A: Pure and Applied Chemistry, vol. 34, Issue 6, 1997.

Renard et al. "Structure of the Repeating Units in the Rhamnogalacturonic Backbone of Apple, Beet and Citrus Pectins," Carbohydrate Research, 275: 115-130 (2005).

Ruiz-Perez et al. "Modulation of Surgical Fibrosis by Microbial Zwitterionic Polysaccharides", 2005, PNAS, 102 (46): 16753-16758.

Wang et al, "Galectin-1 and Galectin-3 in Chronic Pancreatitis," Laboratory Investigation, 80(8): 1233-1241 (2000).

Wert et al. "Increased Metalloproteinase Activity, Oxidant Production, and Emphysema in Surfactant Protein D Gene-inactivated Mice," PNAS. 97: 5972-5977 (2000).

Yamazaki et al, "Simultaneous Induction ofGalectin-3 Phosphorylated on Tyrosine Residue p21 (WAF1/Cipl/Sdil), and the Proliferating Cell Nuclear Antigen at a Distinctive Period of Repair of Hepatocytes Injured by CC14," Biochemical and Biophysical Research Communications. 280(4):1077-1084 (2001).

International Search report and Written Opinion issued in International Application PCT/US2007/069085 mailed Sep. 2, 2008.

Office Action issued in U.S. Appl. No. 11/749,728 mailed on Jun. 1, 2012.

Office Action issued in U.S. Appl. No. 11/749,728 mailed on Feb. 15, 2012.

Office Action issued in U.S. Appl. No. 11/749,728 mailed on May 17, 2010.

Office Action issued in U.S. Appl. No. 11/749,728 mailed on Aug. 21, 2009.

Renard et al., "Structure of the repeating units in the rhamnogalacturonic backbone of apple, beet, and citrus pectins", Carbohydrates Research 275 (1995) pp. 155-165.

Wang et al., "Molecular characterisation of soybean polysaccharides: an approach by size exclusion chromatography, dynamic and static light scattering methods" Carbohydrate Research (2005) vol. 340 pp. 2637-2644.

USP Pharmacopea 28, published Jan. 1, 2005 by United States Pharmacopeal Convention, pp. 1477-1478.

The Merck Manual of Diagnosis and Therapy, Seventeenth Edition, published 1999 by Merck Research Laboratories, pp. 372-374 and 384-386.

Hiramatsu et al., "Improvement of liver fibrosis in chronic hepatitis C patients treated with natural interferon alpha" Journal of Hepatology (1995) vol. 22 pp. 135-142.

Sun et al., "Structural Characterization of a Tobacco Thamnogalacturonan", Carbohydrate Polymers 7 (1987) pp. 143-158.

METHOD FOR TREATMENT OF PULMONARY FIBROSIS

CROSS-REFERENCE TO RELATED APPLICATIONS

This application claims the benefit of and priority to U.S. provisional Application Ser. No. 61/767,057, filed Feb. 20, 2013, the entire disclosure of which is incorporated by reference in its entirety.

FIELD OF THE INVENTION

Methods and compositions of the invention relate compositions and methods for treatment of pulmonary fibrosis.

BACKGROUND OF THE INVENTION

Pulmonary fibrosis is the formation or development of excess fibrous connective tissue (fibrosis) in the lungs. Approximately 5 million people worldwide are affected by pulmonary fibrosis. Pulmonary fibrosis is a fatal disease in which the uncontrolled deposition of extracellular matrix leads to progressive loss of lung function.

SUMMARY OF THE INVENTION

Aspects of the invention relate to novel approaches to treat pulmonary fibrosis.

Aspects of the invention relate to compositions, methods of using and methods of manufacturing compositions capable of treating pulmonary fibrosis.

Other aspects of the invention relate to methods of treating a subject in need thereof. In some embodiments, the method comprises the step of obtaining a composition for parenteral administration, the composition comprising a compound in an acceptable pharmaceutical carrier and administering the composition to a subject in need thereof.

In some embodiments, the compound can be one of galacto-rhamnogalacturonate (GRG), galactoarabino-rhamnogalacturonate (GA-RG), galactomannan (GM), or a combination of any of the foregoing.

In some embodiments, the compound can be a polysaccharide chemically defined as galacto-rhamnogalacturaonate (GRG), a selectively depolymerized branched heteropolymer whose backbone is predominantly comprised of 1,4-linked galacturonic acid (GalA) moieties, with a lesser backbone composition of alternating 1,4-linked GalA and 1,2-linked rhamnose (Rha), which in-turn is linked to any number of side chains, including predominantly 1,4-b-D-galactose (Gal) and 1,5-a-L-arabinose (Ara) residues. Other side chain minor constituents may include xylose (Xyl), glucose (Glu), and fucose (Fuc) or combinations thereof.

In some embodiments, the GRG compound can be produced as described in U.S. Patent Application Publication No. 2008/0107622, now U.S. Pat. No. 8,236,780, which is incorporated expressly by reference for all purposes.

In some embodiments, the GRG compound can be produced as described in U.S. Pat. Nos. 8,128,966, 8,187,624, U.S. Patent Application Publication Nos 2012/0315309 and 2012/0309711 which are incorporated expressly by reference for all purposes.

In some embodiments, the compound can be a polysaccharide chemically defined as galactoarabino-rhamnogalacturonate (GA-RG), a selectively depolymerized, branched heteropolymer whose backbone is predominantly comprised of 1,4-linked galacturonic acid (GalA) moieties, with a lesser backbone composition of alternating 1,4-linked GalA and 1,2-linked rhamnose (Rha), which in-turn is linked to any number of side chains, including predominantly 1,4-b-D-galactose (Gal) and 1,5-a-L-arabinose (Ara) residues. Other side chain minor constituents may include xylose (Xyl), glucose (Glu), and fucose (Fuc) or combinations thereof.

In some embodiments, the GA-RG compound can be produced as described in International Patent Application PCT/US12/55311, and U.S. Patent Application Number US 2013-0261078, which is incorporated expressly by reference for all purposes. In some embodiments, the compound can be a galactomannan (GM) polysaccharide composition produced as described in U.S. Pat. No. 8,236,780 and U.S. Patent Application Publication No. US 2011/0077217 which are incorporated expressly by reference in their entireties for all purposes.

Some aspects of the invention relate to a method comprising obtaining a composition for parenteral or enteral administration comprising a galacto-rhamnogalacturonate in a pharmaceutical acceptable carrier, and administering to a subject in need thereof an effective dose of the composition that results in at least one of the following: at least 5% reduction of lung edema, at least 5% reduction of lung pathology severity scores associated with lung fibrosis, at least 5% reduction of lung tissue hydroxyproline accumulation, at least 5% reduction of expression of pro-inflammatory proteins, at least 5% reduction of expression of fibrogenic proteins. In some embodiments, the administration of the effective dose results in at least 5% improvement of pulmonary function tests including forced vital capacities or oxygen diffusion. In some embodiments, the subject in need has at least one of the following: a primary or secondary lung fibrotic disease.

In some embodiments, the effective dose of galacto-rhamnogalacturonate can be equivalent to an animal dose of about 120 mg/kg. In some embodiments, the effective dose of galacto-rhamnogalacturonate can be equivalent to an animal dose of 10 mg/kg to 180 mg/kg. In some embodiments, the effective dose can be given once, twice or three times weekly.

In some embodiments, the administration of the effective dose results in at least 5% reduction of expression of pro-inflammatory proteins. In some embodiments, the pro-inflammatory proteins can comprise TGF-beta, IL-6, IL-8, IL-13, IP-10, osteopontin, TNF-alpha, CXCL-9/10, VEGF or any combination of the foregoing.

In some embodiments, the administration of the effective dose results in at least 5% reduction of expression of fibrogenic proteins. In some embodiments, the fibrogenic proteins can comprise collagen, elastin or a combination thereof.

In some embodiments, the galacto-rhamnogalacturonate can comprise a 1,4-linked galacturonic acid (GalA) and methyl galacturonate (MeGalA) residues backbone linked to branched heteropolymers of alternating oligomers of α-1,2 linked rhamnose and α-1,4-linked GalA residues, the rhamnose residues carrying a primary branching of oligomers of 1,4-β-D-galactose residues.

In some embodiments, the galacto-rhamnogalacturonate can comprise a 1,4-linked galacturonic acid (GalA) residues backbone linked to branched heteropolymers of alternating oligomers of α-1,2 linked rhamnose and α-1,4-linked GalA residues, the rhamnose residues carrying a primary branching of oligomers of 1,4-β-D-galactose residues.

In some embodiments, the galacto-rhamnogalacturonate can further comprise xylose, glucose, fucose residues or combination thereof.

In some embodiments, the galacto-rhamnogalacturonate can be substantially free of 1,5-α-L-Ara residues.

In some embodiments, the galacto-rhamnogalacturonate is a galactoarabino-rhamnogalacturonate, comprising a 1,4-linked galacturonic acid (GalA) and methyl galacturonate (MeGalA) residues backbone linked to branched heteropolymers of alternating oligomers of α-1,2 linked rhamnose and α-1,4-linked GalA residues, the rhamnose residues carrying a primary branching of oligomers of 1,4-β-D-galactose residues, 1,5-α-L-arabinose residues, or combinations thereof.

In some embodiments, the 1,4-β-D-galactose and 1,5-α-L-arabinose residues are present in a 2:1 or a 3:1 ratio.

In some embodiments, the 1,4-β-D-galactose residues, the 1,5-α-L-arabinose residues or combination thereof can represent at least 10 molar percent of the total molar carbohydrates.

In some embodiments, the galacto-rhamnogalacturonate can have an average molecular weight ranging from 5 kDa to 55 kDa as determined by SEC-RI and/or the SEC-MALLS methods.

In some embodiments, the galacto-rhamnogalacturonate can have an average molecular weight ranging from 2 kDa to 80 kDa as determined by SEC-RI and/or the SEC-MALLS methods.

In some embodiments, the galacto-rhamnogalacturonate can an average molecular weight ranging from 20 kDa to 70 kDa as determined by SEC-RI and/or the SEC-MALLS methods.

In some aspects, the method comprises obtaining a composition for parenteral or enteral administration comprising a galactomannan polysaccharide in a pharmaceutical acceptable carrier, and administering to a subject in need thereof an effective dose of the composition that results in at least one of the following: at least 5% reduction of lung oedema, at least 5% reduction of lung pathology associated with lung fibrosis, at least at least 5% reduction of hydroxyproline accumulation, at least 5% reduction of expression of pro-inflammatory proteins, at least 5% reduction of expression of fibrogenic proteins, wherein the subject in need thereof has at least one of the following: a primary or secondary lung fibrotic disease. In some embodiments, the administration of the effective dose results in at least 5% improvement of pulmonary function tests including forced vital capacities or oxygen diffusion.

In some embodiments, the effective dose of the galactomannan polysaccharide is equivalent to an animal dose of about 60 mg/kg. In some embodiments, the effective dose of the galactomannan polysaccharide is equivalent to an animal dose of 30 mg/kg to 180 mg/kg. In some embodiments, the effective dose can be given once, twice or three times weekly.

In some embodiments, in the step of obtaining, the galactomannan polysaccharide has a mannose to galactose ratio ranging from 1:1 to 1:4.

In some embodiments, in the step of obtaining, the galactomannan polysaccharide has a mannose to galactose ratio of 1.7:1.

In some embodiments, in the step of obtaining, the galactomannan polysaccharide has a molecular weight of about 48,000 D.

In some embodiments, in the step of obtaining, the galactomannan polysaccharide has average molecular weight ranging from 4,000 D to 60,000 D.

In some embodiments, the administration of the effective dose results in at least 5% reduction of expression of pro-inflammatory proteins. In some embodiments, the pro-inflammatory proteins can comprise TGF-beta, IL-6, IL-8, IL-13, IP-10, osteopontin, TNF-alpha, CXCL-9/10, VEGF or any combination of the foregoing.

In some embodiments, the administration of the effective dose results in at least 5% reduction of expression of fibrogenic proteins. In some embodiments, the fibrogenic proteins can comprise collagen, elastin or a combination thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will be further explained with reference to the attached drawings, wherein like structures are referred to by like numerals throughout the several views. The drawings shown are not necessarily to scale, with emphasis instead generally being placed upon illustrating the principles of the present invention.

FIG. 1A shows the daily weight change of mice expressed as mean and standard error of the mean. FIG. 1B shows the percent change in weight for each treatment group as calculated using the area under the curve (AUC).

DETAILED DESCRIPTION OF THE INVENTION

Figure 1A:
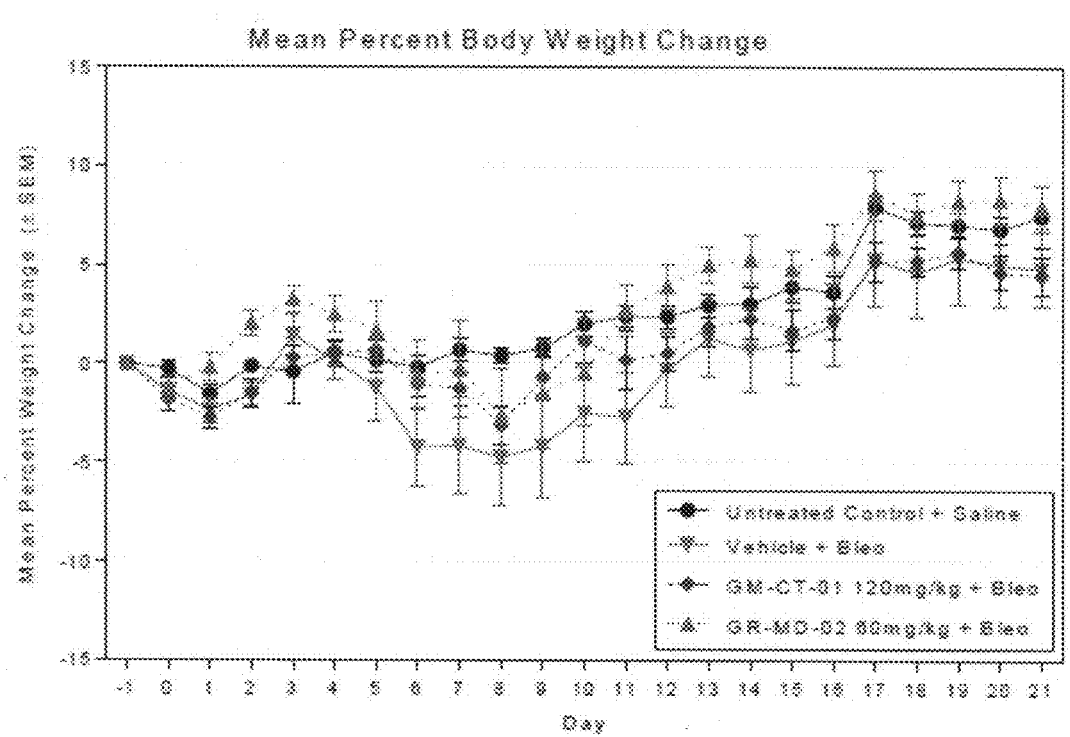
FIGS. 1A and 1B depicts the change in animal weight in the mouse model of bleomycin-induced pulmonary fibrosis with early treatment with GR-MD-02 and GM-CT-01.

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Citation of documents herein is not intended as an admission that any of the documents cited herein is pertinent prior art, or an admission that the cited documents are considered material to the patentability of the claims of the present application.

Unless otherwise specified, all percentages expressed herein are weight/weight.

Aspects of the invention relate to novel approaches to treat pulmonary fibrosis using a complex carbohydrate pharmaceutical product or other agents described herein. In some embodiments, the methods disclosed herein relate to the treatment of a subject having a primary or secondary lung fibrotic disease.

Galectins

Galectins (also known as galaptins or S-lectin) are a family of lectins which bind beta-galactoside. Galectin as general name was proposed in 1994 for a family of animal lectins (Barondes, S. H., et al.: Galectins: a family of animal beta-galactoside-binding lectins. Cell 76, 597-598, 1994), The family is defined by having at least one characteristic carbohydrate recognition domain (CRD) with an affinity for beta-galactosides and sharing certain sequence elements. Within the same peptide chain, some galectins have a CRD with only a few additional amino acids, whereas others have two CRDs joined by a link peptide, and one (galectin-3) has one CRD joined to a different type of domain. The galectin carbohydrate recognition domain (CRD) is a beta-sandwich of about 135 amino acids. The two sheets are slightly bent with 6 strands forming the concave side and 5 strands forming the convex side. The concave side forms a groove in which carbohydrate is bound (Leffler H, Carlsson S, Hedlund M, Qian Y, Poirier F (2004). "Introduction to galectins". Glycoconj. J. 19 (7-9): 433-40).

A wide variety of biological phenomena have been shown to be related to galectins, e.g., development, differentiation, morphogenesis, tumor metastasis, apoptosis, RNA splicing, etc. However, relatively little is known about the mechanism by which galectins exert these functions, particularly in terms of carbohydrate recognition.

Generally, the carbohydrate domain binds to galactose residues associated with glycoproteins. At least fifteen mammalian galectin proteins have been identified which have one or two carbohydrate domain in tandem.

Galectin proteins are found in the intracellular space where they have been assigned a number of functions and are secreted into the extracellular space. In the extracellular space, galectin proteins can have multiple functions including promoting interactions between glycoproteins that may lead to reduced function, or enhanced functions, or in the case of integral membrane glycoprotein receptors, modification of cellular signaling (Sato et al "Galectins as danger signals in host-pathogen and host-tumor interactions: new members of the growing group of "Alarmins." In "Galectins," (Klyosov, et al eds.), John Wiley and Sons, 115-145, 2008, Liu et al "Galectins in acute and chronic inflammation," Ann. N. Y. Acad. Sci. 1253: 80-91, 2012). Galectin proteins in the extracellular space can additionally promote cell-cell and cell matrix interactions (Wang et al., "Nuclear and cytoplasmic localization of galectin-1 and galectin-3 and their roles in pre-mRNA splicing." In "Galectins" (Klyosov et al eds.), John Wiley and Sons, 87-95, 2008).

Galectins have been shown to have domains which promote homodimerization. Thus, galectins are capable of acting as a "molecular glue" of sorts between glycoproteins. Galectins are found in multiple cellular compartments, including the nucleus and cytoplasm, and are secreted into the extracellular space where they interact with cell surface and extracellular matrix glycoproteins. The mechanism of molecular interactions can depend on the localization. While galectins can interact with glycoproteins in the extracellular space, the interactions of galectin with other proteins in the intracellular space generally occurs via protein domains. In the extracellular space the association of cell surface receptors may increase or decrease receptor signaling or the ability to interact with ligands. Galectin proteins are markedly increased in a number of animal and human disease states, including but not limited to diseases associated with inflammation, fibrosis, autoimmunity, and neoplasia. Galectins have been directly implicated in the disease pathogenesis, as described below. For example, diseases states that may be dependent on galectins include, but are not limited to, acute and chronic inflammation, allergic disorders, asthma, dermatitis, autoimmune disease, inflammatory and degenerative arthritis, immune-mediated neurological disease, fibrosis of multiple organs (including but not limited to liver, lung, kidney, pancreas, and heart), inflammatory bowel disease, atherosclerosis, heart failure, ocular inflammatory disease, a large variety of cancers.

In addition to disease states, galectins are important regulatory molecules in modulating the response of immune cells to vaccination, exogenous pathogens and cancer cells.

One of skill in the art will appreciate that compounds that can bind to galectins and/or alter galectin's affinity for glycoproteins, reduce hetero- or homo-typic interactions between galectins, or otherwise alter the function, synthesis, or metabolism of galectin proteins may have important therapeutic effects in galectin-dependent diseases.

Galectins show an affinity for galactose residues attached to other organic compounds, such as in lactose [(β-D-Galactosido)-D-glucose], N-acetyl-lactosamine, poly-N-acetyllactosamine, galactomannans, fragments of pectins, as well as other galactose containing compounds. It should be noted that galactose by itself does not bind to galectins, or binds so weakly that the binding can hardly be detected.

Pectin and modified pectin have been shown to bind to galectin proteins presumably on the basis of containing galactose residues that are presented in the context of a macromolecule, in this case a complex carbohydrate rather than a glycoprotein in the case of animal cells.

Galectin proteins have been shown to be markedly increased in inflammation, fibrotic disorders, and neoplasia (Ito et al. "Galectin-1 as a potent target for cancer therapy: role in the tumor microenvironment", Cancer Metastasis Rev. PMID: 22706847 (2012), Nangia-Makker et al. Galectin-3 binding and metastasis," Methods Mol Biol. 878: 251-266, 2012, Canesin et al. Galectin-3 expression is associated with bladder cancer progression and clinical outcome," Tumour Biol. 31: 277-285, 2010, Wanninger et al. "Systemic and hepatic vein galectin-3 are increased in patients with alcoholic liver cirrhosis and negatively correlate with liver function," Cytokine. 55: 435-40, 2011. Moreover, experiments have shown that galectins, particularly galectin-1 and galectin-3, are directly involved in the pathogenesis of these classes of disease (Toussaint et al., "Galectin-1, a gene preferentially expressed at the tumor margin, promotes glioblastoma cell invasion.", Mol Cancer. 11:32, 2012, Liu et al 2012, Newlaczyl et al., "Galectin-3—a jack-of-all-trades in cancer," Cancer Lett. 313: 123-128, 2011, Banh et al., "Tumor galectin-1 mediates tumor growth and metastasis through regulation of T-cell apoptosis," Cancer Res. 71: 4423-31, 2011, Lefranc et al., "Galectin-1 mediated biochemical controls of melanoma and glioma aggressive behavior," World J. Biol. Chem. 2: 193-201, 2011, Forsman et al., "Galectin 3 aggravates joint inflammation and destruction in antigen-induced arthritis," Arthritis Reum. 63: 445-454, 2011, de Boer et al., "Galectin-3 in cardiac remodeling and heart failure," Curr. Heart Fail. Rep. 7, 1-8, 2010, Ueland et al., "Galectin-3 in heart failure: high levels are associated with all-cause mortality," Int J Cardiol. 150: 361-364, 2011, Ohshima et al., "Galectin 3 and its binding protein in rheumatoid arthritis," Arthritis Rheum. 48: 2788-2795, 2003).

The term "effective dose" means the amount of the GRG, GA-RG, GM, compounds described herein when administered as a parental dose to an animal or human result in at least 5% decrease of a chosen molecular marker.

In some embodiments, the effective dose of galacto-rhamnogalacturonate can be equivalent to an animal dose of about 120 mg/kg. In some embodiments, the effective dose of galacto-rhamnogalacturonate can be equivalent to an animal dose of 10 mg/kg to 180 mg/kg. In some embodiments, the effective dose of the galactomannan polysaccharide is equivalent to an animal dose of about 60 mg/kg. In some embodiments, the effective dose of the galactomannan polysaccharide is equivalent to an animal dose of 30 mg/kg to 180 mg/kg. In some embodiments, the effective dose can be given once, twice or three times weekly.

The term "efficacy" means demonstrating an improvement of lung fibrosis of at least 10% using treatment with the GRG, GA-RG, or GM compounds described herein as compared to treatment with vehicle-treated subject.

Other aspects of the invention relate to methods of treating a subject in need thereof. In some embodiments, the method comprises the step of obtaining a composition for intravenous or subcutaneous administration comprising a compound in an acceptable pharmaceutical carrier.

In some embodiments, the compound is a polysaccharide chemically defined as galacto-rhamnogalacturonate (GRG), a selectively depolymerized, branched heteropolymer whose backbone is predominantly comprised of 1,4-linked galacturonic acid (GalA) moieties, with a lesser backbone composition of alternating 1,4-linked GalA and 1,2-linked rhamnose (Rha), which in-turn is linked to any number of side chains, including predominantly 1,4-b-D-galactose (Gal) and 1,5-a-L-arabinose (Ara) residues. Other side chain minor constituents may include xylose (Xyl), glucose (Glu), and fucose (Fuc) or combinations thereof.

In some embodiments, the GRG compound is produced as described in U.S. Pat. No. 8,236,780, which are incorporated expressly by reference for all purposes.

In some embodiments, the GRG compound can be produced as described in U.S. Pat. Nos. 8,128,966, 8,187,624, U.S. Patent Application Publication Nos 2012/0315309 and 2012/0309711 which are incorporated expressly by reference for all purposes.

In some embodiments, the compound is a polysaccharide chemically defined as galactoarabino-rhamnogalacturonate (GA-RG), a selectively depolymerized, branched heteropolymer whose backbone is predominantly comprised of 1,4-linked galacturonic acid (GalA) moieties, with a lesser backbone composition of alternating 1,4-linked GalA and 1,2-linked rhamnose (Rha), which in-turn is linked to any number of side chains, including predominantly 1,4-b-D-galactose (Gal) and 1,5-a-L-arabinose (Ara) residues. Other side chain minor constituents may include xylose (Xyl), glucose (Glu), and fucose (Fuc) or combinations thereof.

In some embodiments, the GA-RG compound is produced as described in International Patent Application PCT/US12/55311, which is incorporated expressly by reference for all purposes.

In some embodiments, the molar percent of the 1,4-b-D-Gal and 1,5-a-L-Ara residues in the GA-RG compound of the present invention is 21.5% with a molar ratio of 3:1 of 1,4-b-D-Gal to 1,5-a-L-Ara.

In some embodiments, the compound is a polysaccharide chemically defined as galactoarabino-rhamnogalacturonate (GA-RG), with a molecular weight range of 20,000 to 70,000 Daltons as determined by SEC-RI method.

In some embodiments, the compound is a galactomannan (GM) polysaccharide composition produced as described in U.S. Patent Application US20110077217, incorporated expressly by reference in its entirety for all purposes.

In some embodiments, the average molecular weight of the GM compound is approximately 4,000 and 60,000 Da, as determined by the SEC-MALLS method.

In some embodiments, the complex carbohydrate compounds described herein can target secreted and membrane-associated galectins, for example galectin-3.

In some embodiments, if an inducer of fibrosis, such bleomycin administered by intra-tracheal instillation, causes formation of the biochemical markers, but a concurrent administration of the inducer and a suitable complex carbohydrate compounds including but not limited to GM, GR, or GA-RG, does not lead to formation of the same marker, or leads to formation of the same marker but in a reduced amount, the polysaccharide prevents or slows down fibrosis.

Some aspects of the invention relate to a method of treating a patient at risk of pulmonary fibrosis. The method comprises administering to a patient a pharmaceutical composition comprising the carbohydrate compounds described herein in an amount sufficient to reduce the risk of developing pulmonary fibrosis. Other aspects of the invention relate to method of treating pulmonary fibrosis. The method comprises administering to a patient a pharmaceutical composition comprising the carbohydrate compounds described herein in an amount sufficient to reduce significantly one or more of the following: lung oedema, lung pathology associated with lung fibrosis, hydroxyproline accumulation, and expression of pro-inflammatory proteins, such as TGF-beta, IL-6, IL-8, IL-13, IP-10, osteopontin, TNF-alpha, CXCL-9/10, VEGF, and fibrogenic proteins, such as collagen and, elastin.

In some embodiments, the administration of the compound results in at least 5% reduction of lung oedema, at least 5% reduction of lung pathology associated with lung fibrosis, at least at least 5% reduction of hydroxyproline accumulation, at least 5% reduction of expression of pro-inflammatory proteins, at least 5% reduction of expression of fibrogenic proteins, wherein the subject in need thereof has at least one of the following: a primary or secondary lung fibrotic disease. In some embodiments, the administration of the effective dose results in at least 5% improvement of pulmonary function tests including forced vital capacities or oxygen diffusion.

EXAMPLE

Mouse Model

Example 1

Early Treatment of Pulmonary Fibrosis Induced by Bleomycin in C57Bl/6 Mice

Instillation of bleomycin in the trachea induces changes similar to diffuse pulmonary fibrosis and/or fibrosing alveolitis in humans. There is an increase in deposition and net synthesis of collagen in the lung with this model.

This mouse model of pulmonary fibrosis is used extensively in pre-clinical evaluation of drugs, as indicated in a review that reports on 240 individual studies (Int J of Biochem & Cell Biology 40 (2008) 362-382)

This model can be used to evaluate therapy started in the inflammatory phase of the belomycin insult (started <7 day after bleomycin) or after the inflammatory phase and during fibrogenesis (started >7 day after bleomycin). In this example, early therapy was evaluated.

The GM (GM-CT-01) and GA-RG (GR-MD-02) compounds were evaluated as preventative therapy in this mouse model.

GM-CT-01 is a galactomannan (GM) isolated from seeds of *Cyamopsis tetragonoloba*, or Guar gum, and subjected to a controlled partial chemical degradation. A backbone of the galactomannan is composed of (1→4)-linked β-D-mannopyranosyl units, to which single α-D-galactopyranosyl is attached by (1→6)-linkage. Chemical names of the galactomannan are 1,4-β-D-Galactomannan, or [(1→6)-α-D-galacto-(1→4)-β-D-mannan]. The average repeating unit of GM-CT-01 consists of seventeen β-D-Man residues and ten α-D-Gal residues (Man/Gal ratio is 1.7), and an average polymeric molecule contains approximately 12 of such repeating units (for the average molecular weight ranging from 42,000 Da through 60,000 Da).

GR-MD-02 is a galactoarabino-rhamnogalacturonate (GARG), a selectively depolymerized, branched heteropolymer whose backbone is predominantly comprised of 1,4-linked galacturonic acid (GalA) moieties, with a lesser backbone composition of alternating 1,4-linked GalA and 1,2-linked rhamnose (Rha), which in-turn is linked to any number of side chains, including predominantly 1,4-b-D-galactose (Gal) and 1,5-a-L-arabinose (Ara) residues. Other side chain minor constituents may include xylose (Xyl), glucose (Glu), and fucose (Fuc) or combinations thereof. The GR-MD-02 has an average molecular weight ranging from 20,000 Da to 70,000 Da.

Pulmonary fibrosis was induced in animals using intra-tracheal instillation of bleomycin at 2.25 U/kg. Animals were treated using a GM compound (GM-CT-01) or GA-RG compound (GR-MD-02) delivered by intravenous infusion as described in Table 1.

TABLE 1

| Group Number | Number of Animals | Bleomycin Dose (Day 0) | Treatment (IV) | Test Article Dosing |
|---|---|---|---|---|
| 1 | 10 | Saline | — | — |
| 2 | 12 | 2.25 U/kg | Vehicle | QD Days: −1, 2, 6, 9, 13, 16, 20 |
| 3 | 12 | 2.25 U/kg | GM-CT-01 120 mg/kg | QD Days: −1, 2, 6, 9, 13, 16, 20 Days |
| 4 | 12 | 2.25 U/kg | GR-MD-02 60 mg/kg | Days: −1, 2, 6, 9, 13, 16, 20 |

Figure 1B:
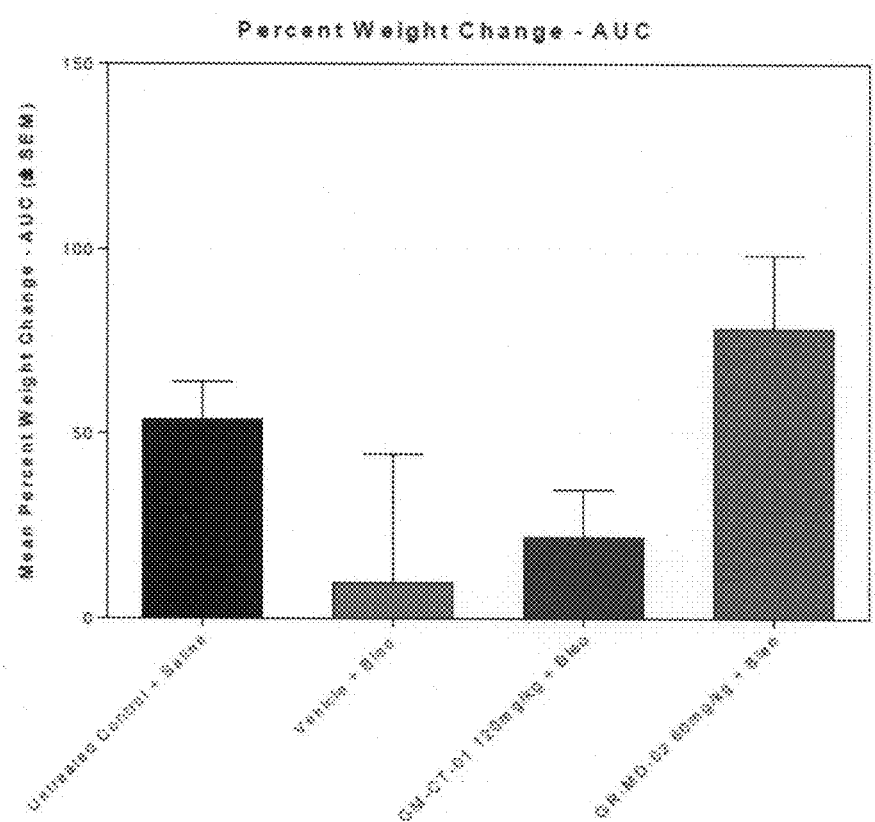

Animals were evaluated for their weight loss (FIG. 1A-B). While there appeared to be a qualitative difference in weight loss between some groups, quantitative analysis of area under the curve showed no difference between groups.

Figure 2:
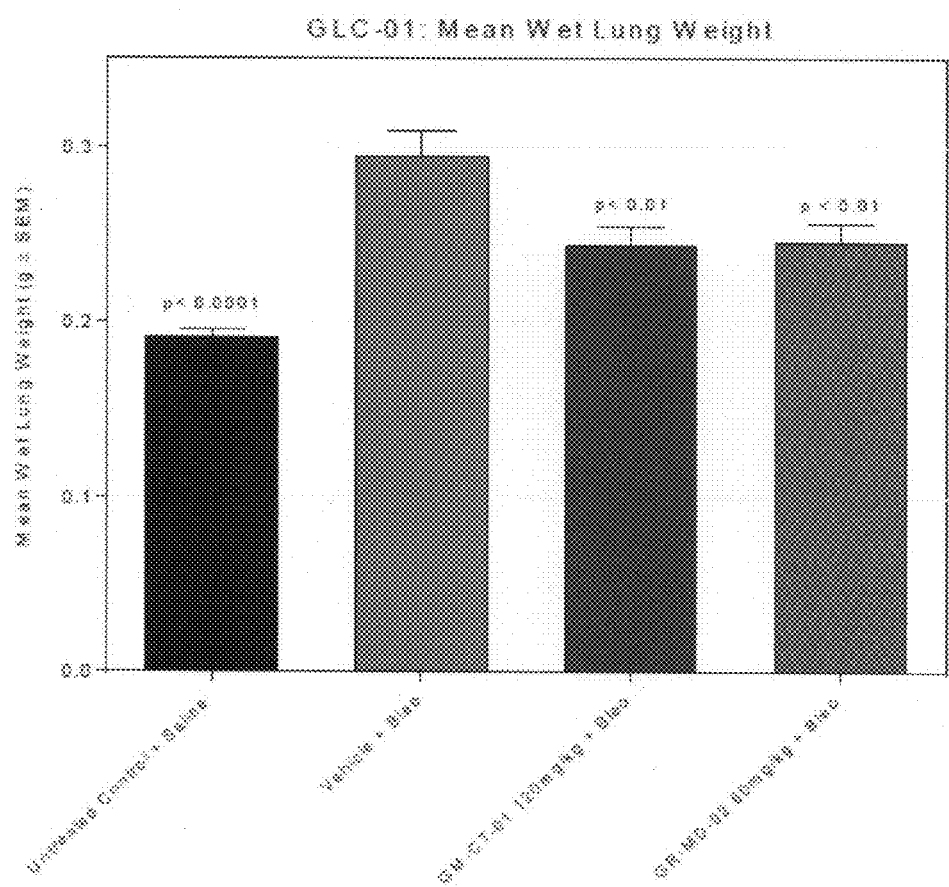
FIG. 2 is a graph showing the mean lung wet weight on day 21 in treated and control groups, according to one embodiment of the invention.

Animals were euthanized on Day 21 and the lungs were weighed. Data shown in FIG. 2 represent group means and SEM. Statistical comparison among all groups was performed using one-way ANOVA with Newman-Keuls multiple comparison test. Both the GM-CT-01 and the GR-MD-02 compounds were shown to significantly reduce lung weight in comparison to vehicle-treated mice.

Figure 3:
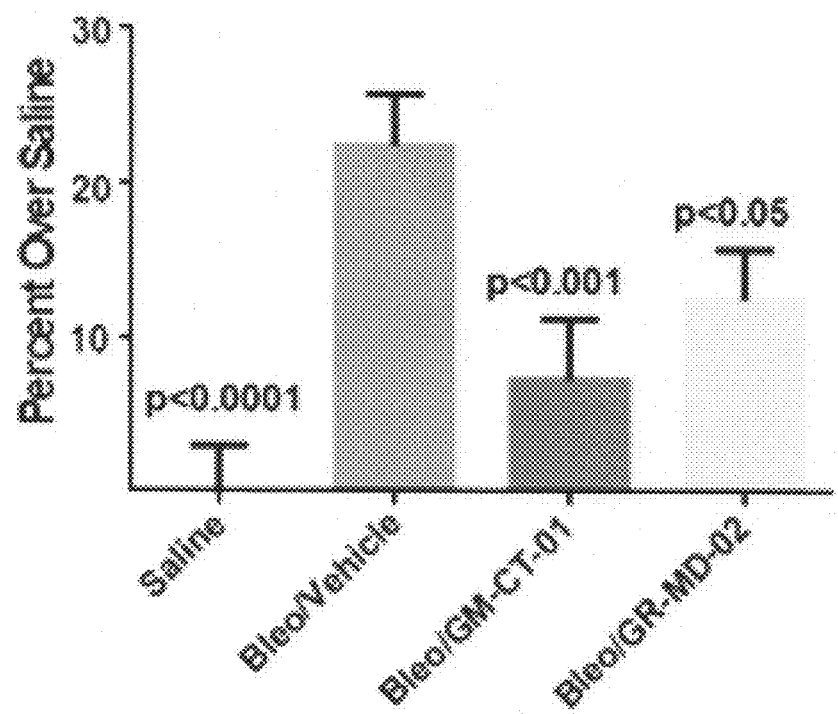
FIG. 3 is a graph showing the mean total lung hydroxyproline content (expressed as a percent of saline treated mice) in mice on day 21 in treated and control groups, according to one embodiment of the invention.

After euthanasia, the total lung hydroxyproline content was measured. Data shown in FIG. 3 represent group mean and SEM and expressed as microgram of hydroxyproline per mg of lung tissue. Statistical comparison to the "vehicle+Bleomycin" group was performed using one-way ANOVA with Holm-Sidak's multiple comparison test. Both the GM-CT-01 and the GA-MD-02 compounds were shown to reduce lung hydroxyproline content compared to vehicle-treated control mice.

Figure 4:
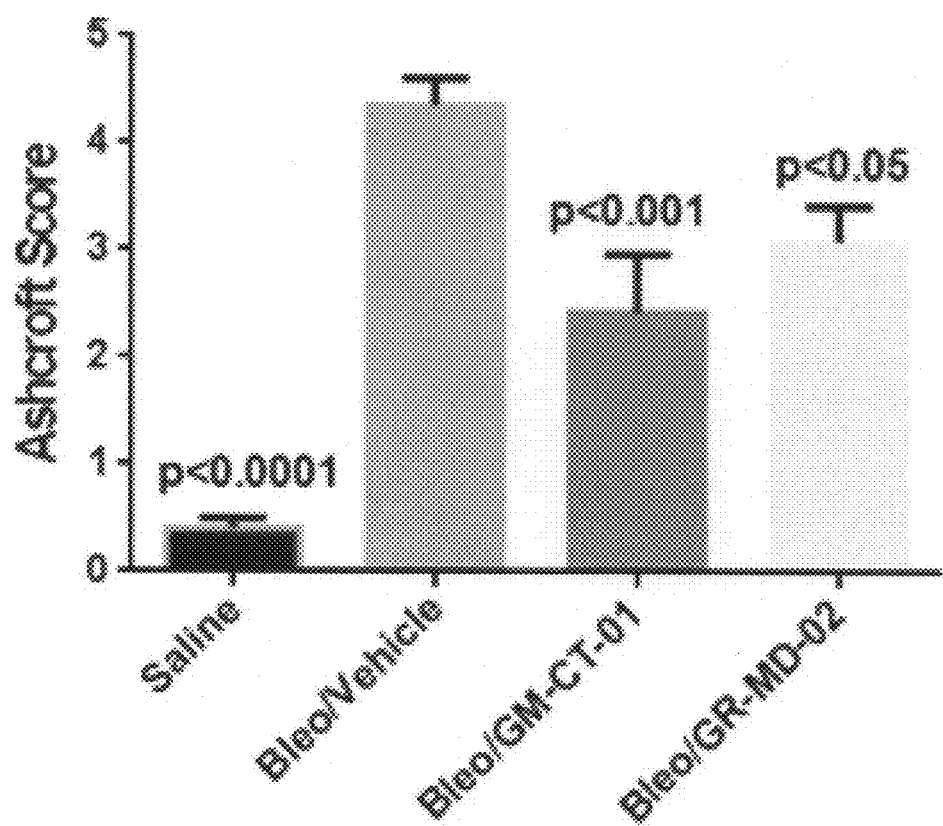
FIG. 4 is a graph showing the modified Ashcroft lung fibrosis index scores in treated and control groups, according to one embodiment of the invention.

The Modified Ashcroft Index score was determined for the vehicle-treated control mice and the GR-MD-02 and GM-CT-01 treated mice. FIG. 4 shows the Modified Ashcroft Index score with outliers removed. There were two notable outliers. One vehicle-treated control mice was essentially not affected by bleomycin administration. In the GR treatment group, there was one animal with severe fibrosis. If these two animals are removed from the analysis, there is a significant different between vehicle and GR-MD-02 treated animals ($p=0.0112$, unpaired t-test). There is also a significant difference between mice and GM-CT-01 treated animals ($p=0.0199$, unpaired West).

Figure 5:
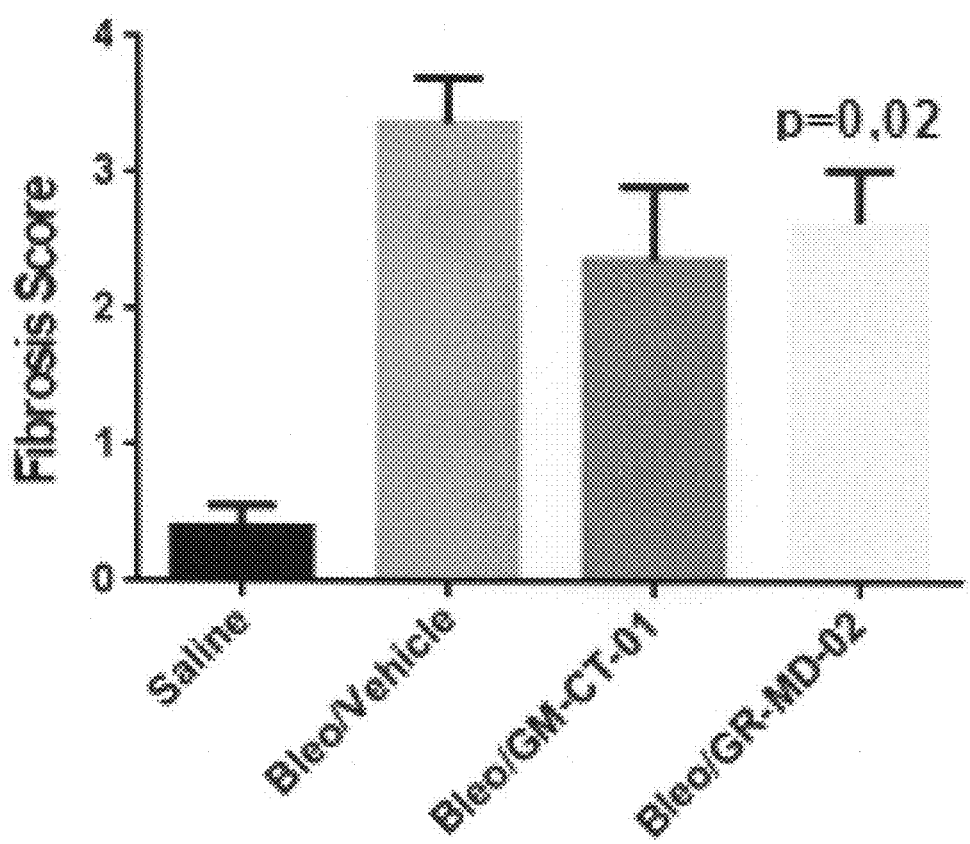
FIG. 5 is a graph showing the general pulmonary fibrosis scores on treated and control groups, according to one embodiment of the invention.

The general fibrosis score was determined. FIG. 5 shows the general fibrosis score with outliers removed. There were two notable outliers. One vehicle-treated control mice was essentially not affected by bleomycin administration. In the GR-MD-02 treatment group, there was one animal with severe fibrosis. If these two animals are removed from the analysis, there is a significant different between vehicle and GR-MD-02 treated animals ($p=0.0206$, unpaired t-test) and GM-CT-01 treatment approaches significance ($p=0.0979$, unpaired t-test).

Figure 6:
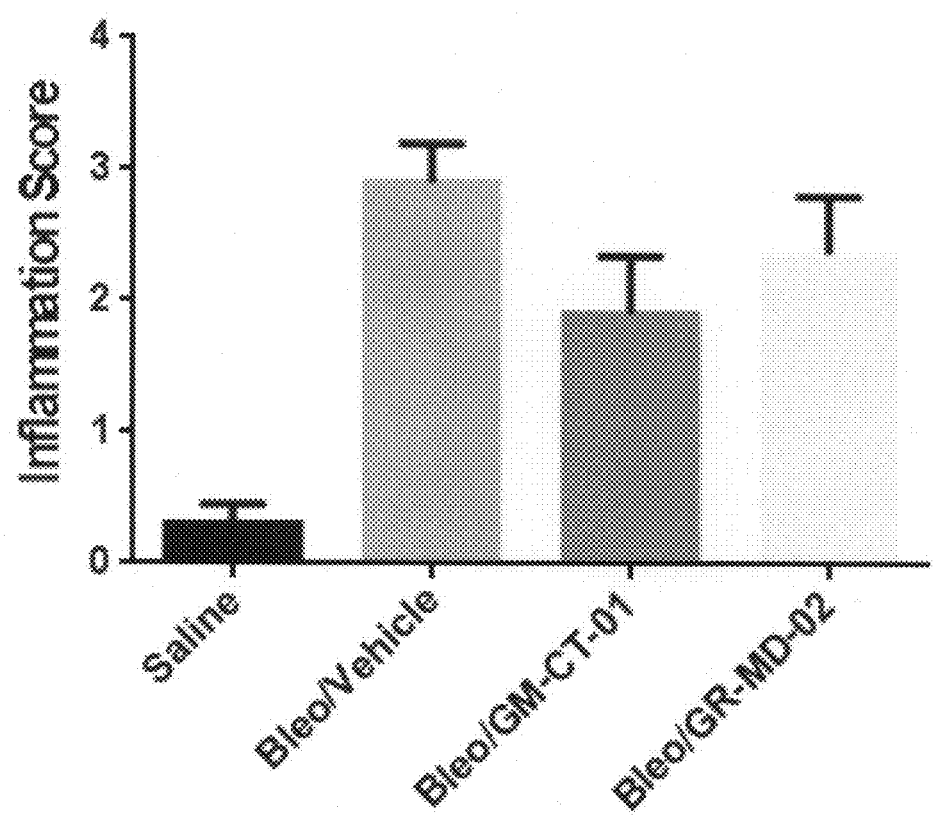
FIG. 6 is a graph showing the inflammation scores on treated and control groups, according to one embodiment of the invention.

Inflammation score was determined. FIG. 6 shows the Inflammation score with outliers removed. There were two notable outliers. One vehicle-treated control mice was essentially not affected by bleomycin administration. In the GR-MD-02 treatment group, there was one animal with severe fibrosis. If these two animals are removed from the analysis, then both treatment approach significance (GM-CT-01 vs. vehicle, $p=0.0544$ unpaired t-test and GR-MD-02 vs. vehicle, $p=0.0508$, unpaired t-test).

Figure 7:
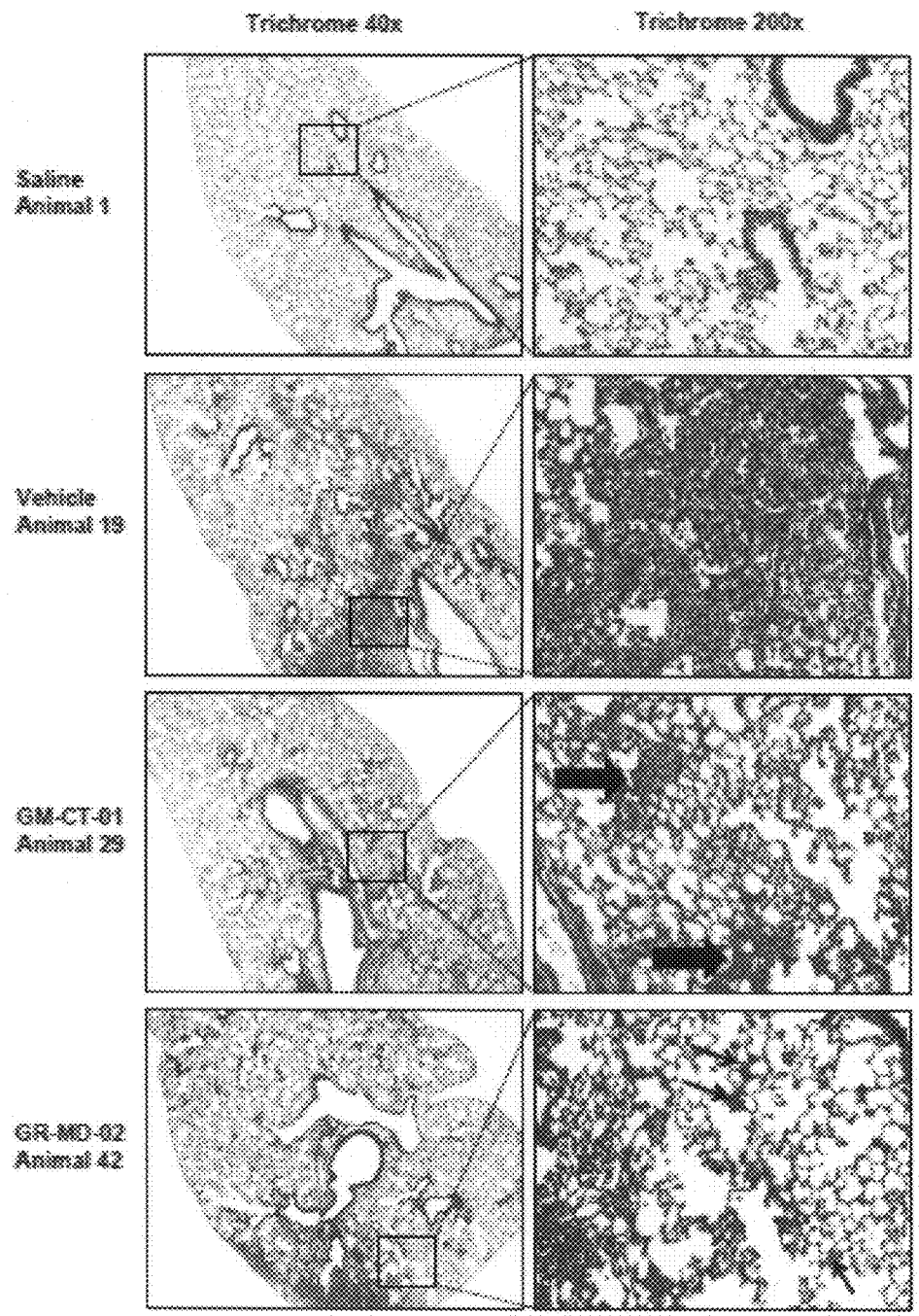
FIG. 7 are representative photomicrographs with trichrome from treated and control groups, according to one embodiment of the invention.

Lung pathology with trichrome stain of saline control, vehicle+bleomycin, GM-CT-01 and GR-MD-02 treated animals was examined. All tissue samples were examined and examples are shown in FIG. 7. Both GM-CT-01 and GR-MD- 02 treatment were found to be effective at reducing fibrosis. Both the number of animals with fibrosis and the average degree of fibrosis were reduced with both treatments. Vehicle-treated animals tended to have contiguous areas of fibrosis affecting large areas of most lung lobes. Fibrous connective tissue stains blue with trichrome and is visualized as steaming blue fibers (asterisks, vehicle-treated animal, FIG. 7). With both treatments, animals had smaller areas of fibrosis. There were often small knot-like formations (arrows, GR-MD-02 treated animal, FIG. 7) or small masses (thick arrows, GM-CT-01 treated animal, FIG. 7) of fibrosis, but these tended not to aggregate to the large formation seen in the vehicle-treated animals and to affect a smaller percentage of lungs.

Figure 8:
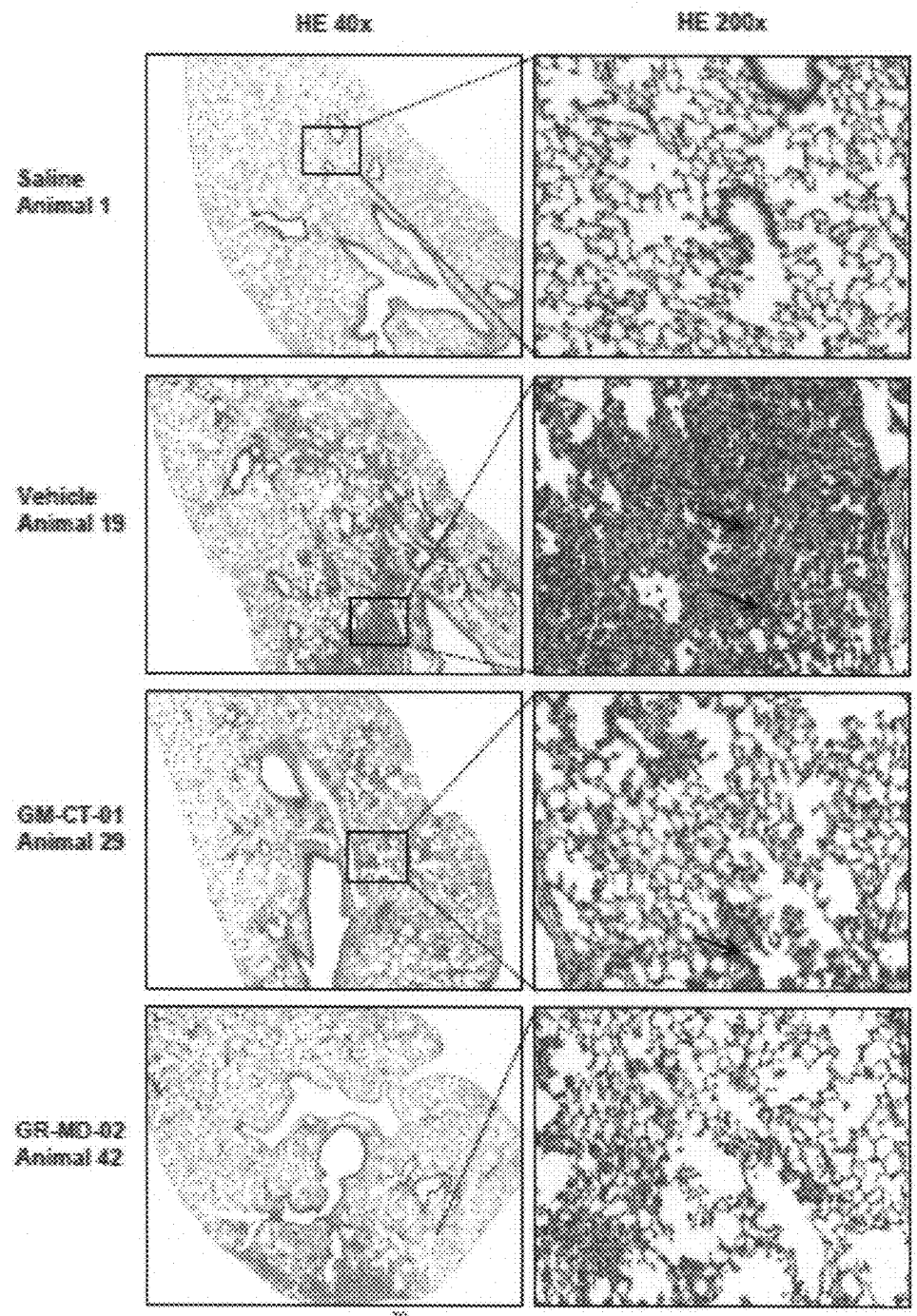
FIG. 8 are representative photomicrographs with H & E from treated and control groups, according to one embodiment of the invention.

Representative images with H & E are shown in FIGS. 8. H & E images show the same basic features as those stained with the trichrome stain. There are mixed mononuclear cell infiltrate associated with the fibrosis. This inflammation is more clearly evident with the HE stain (arrows, FIG. 8).

The foregoing results showed that treatment with GM (GM-CT-01) and GA-RG (GR-MD-02) caused a significant reduction in mean lung weight and lung hydroxyproline content compared to the vehicle-treated control group.

Histologic analysis indicated that GM-CT-01 and GR-MD-02 produced a significant reduction in the Modified Ashcroft Index Score compared to the vehicle group.

Although the rest of the histological findings were not statistically significant, there were clear, notable trends suggesting a positive treatment effect for both drugs.

The results with the GM compound (GM-CT-01) and the GA-RG compound (GR-MD-02) are superior to the results using pirfenadone which is a small molecule comprising a modified phenyl pyridine. The results with GR-MD-02 were found to be similar to treatment with anti-TGFbeta, and the results with GM-CT-01 were found to be superior to treatment with anti-TGFbeta in the experience of the laboratory.

Example 2

Late Treatment of Pulmonary Fibrosis Induced by Bleomycin in C57Bl/6 Mice

In these experiments, treatment was initiated after the time when the inflammatory reaction is known to have subsided and the process is one of primarily fibrogenesis. Pulmonary fibrosis was induced in animals using bleomycin at 2.25 U/kg at day 0 as described above. Animals were treated using a GM compound intravenously (GM-CT-01) or GA-RG compound intravenously (GR-MD-02) as described in Table 2.

TABLE 2

| Group Number | Number of Animals | Bleomycin Dose (Day 0) | Treatment | Route | Test Article Dosing Schedule |
|---|---|---|---|---|---|
| 1 | 10 | Saline | — | — | — |
| 2 | 12 | 2.25 U/kg | Vehicle | IV | QD Days: 10, 13, 16, 20 |
| 3 | 12 | 2.25 U/kg | GM-CT-01 120 mg/kg | IV | QD Days: 10, 13, 16, 20 |
| 5 | 12 | 2.25 U/kg | GR-MD-02 60 mg/kg | IV | QD Days: 10, 13, 16, 20 |

Figure 9:
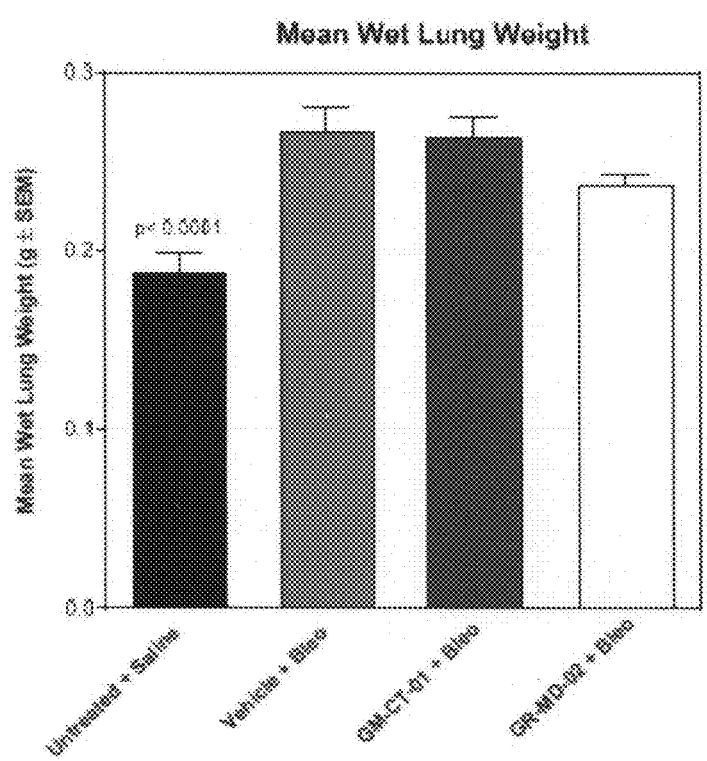
FIG. 9 is a graph showing the weights of the lung of the control groups, vehicle treated group, and treated groups.

Animals were euthanized on Day 21 and the lungs were weighed. Data shown in FIG. 9 represent group means and standard error of the means. While there was a decreased lung weight of the GR-MD-02 treated group as compared to control animals, this difference did not reach statistical significance.

Figure 10:
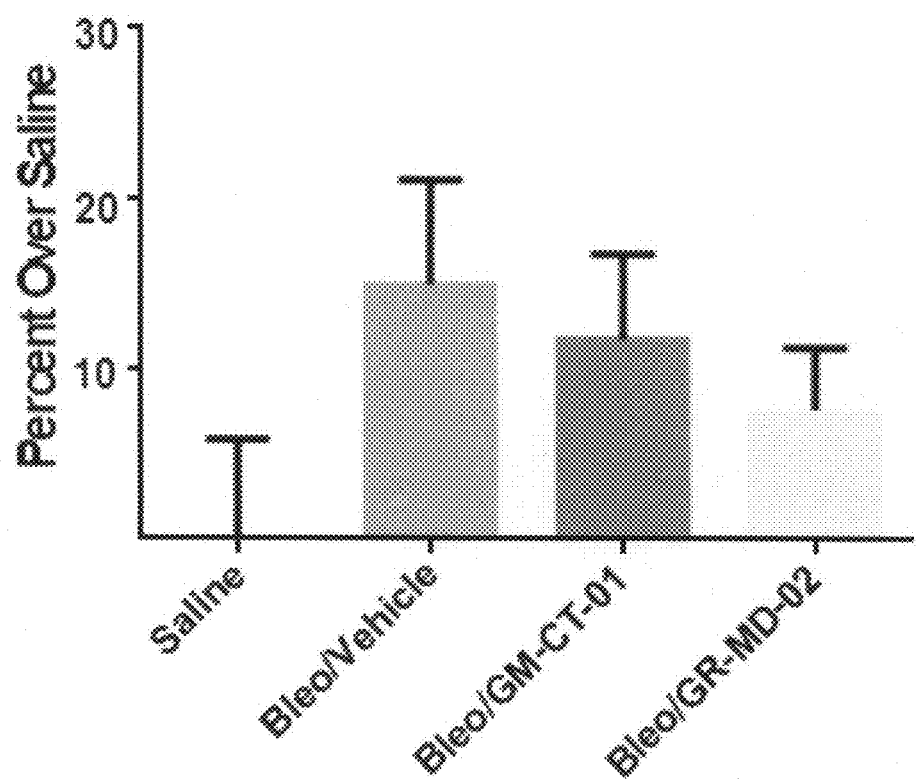
FIG. 10 is a graph showing the lung hydroxyproline (expressed as a percent of saline treated mice) of the control groups, vehicle treated group, and treated groups.

The total lung hydroxyproline content was measured. Data shown in FIG. 10 represent group mean and expressed as microgram of hydroxyproline per mg of lung tissue. Treatment with GR-MD-02 reduced the increase in hydroxyproline by 50%, but because of the variability in the data, this difference did not reach significance. There was less of a decrease in GM-CT-01 animals.

Figure 11:
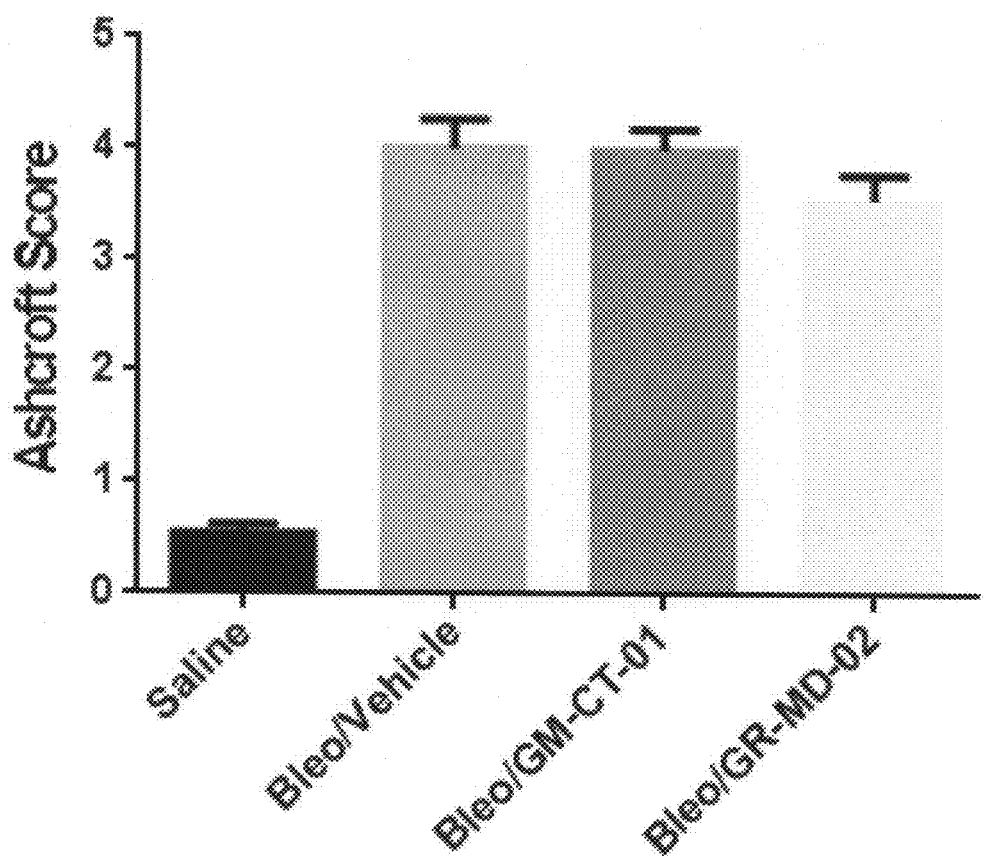
FIG. 11 is a graph showing the Aschroft fibrosis index score from a histology assessment of the control groups, vehicle treated group, and treated groups.

The Modified Ashcroft Index score was determined for the vehicle-treated control mice and the GR-MD-02 and GM-CT-0-treated mice. FIG. 11 shows the Aschroft score. There was a reduction in the Aschroft score in the GR-MD-02 treated animals as compared to vehicle treated animals, but the change did not reach significance. There was little change in the GM-CT-01 treated group.

Figure 12:
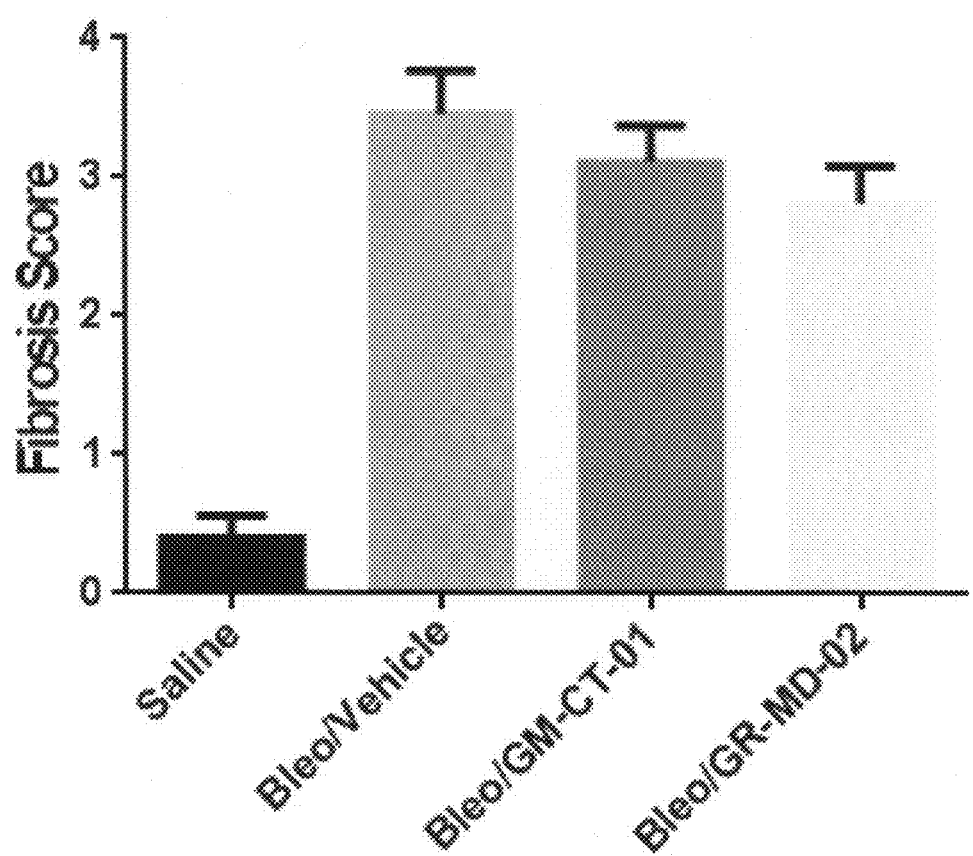
FIG. 12 is a graph showing the general fibrosis score from a histology assessment of the control groups, vehicle treated group, and treated groups.

FIG. 12 shows the general fibrosis score for each animal group. There was a reduction in the fibrosis score in animals treated with both GM-CT-01 and GR-MD-02 as compared to the vehicle-treated animals, but the differences did not reach statistical significance.

Figure 13:
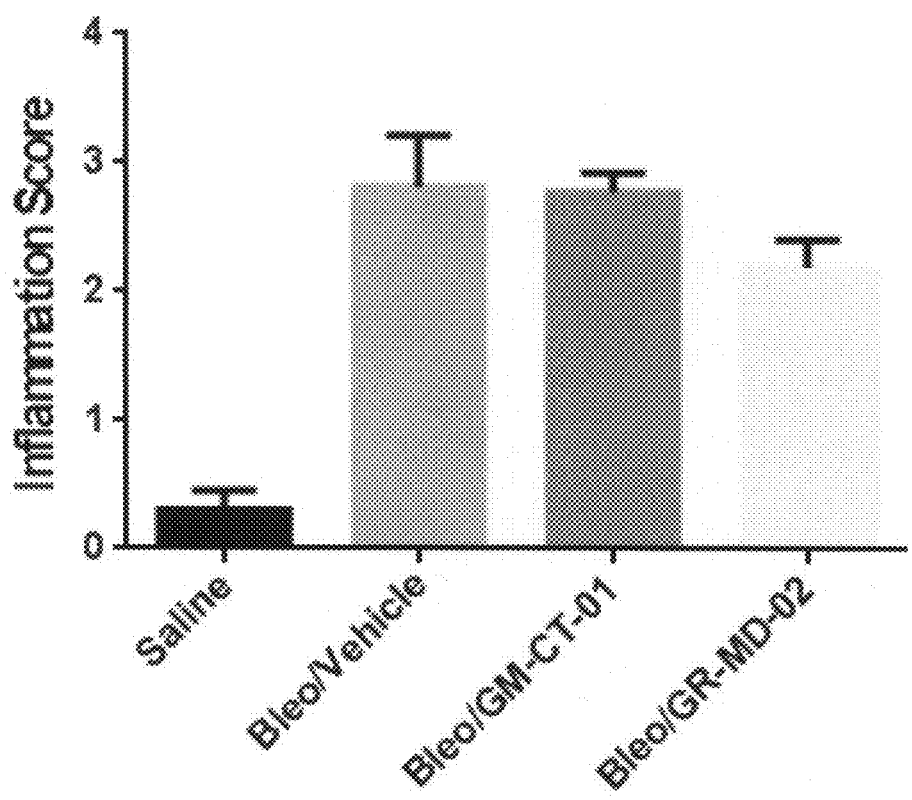
FIG. 13 is a graph showing the inflammation score from a histology assessment of the control groups, vehicle treated group, and treated groups.

FIG. 13 shows the Inflammation score for each animal group. There was a reduction in inflammation score in the group treated with GR-MD-02 as compared to vehicle controls, but no change in the GM-CT-01 group as compared to vehicle control. The differences seen were not statistically significant.

Figure 14:
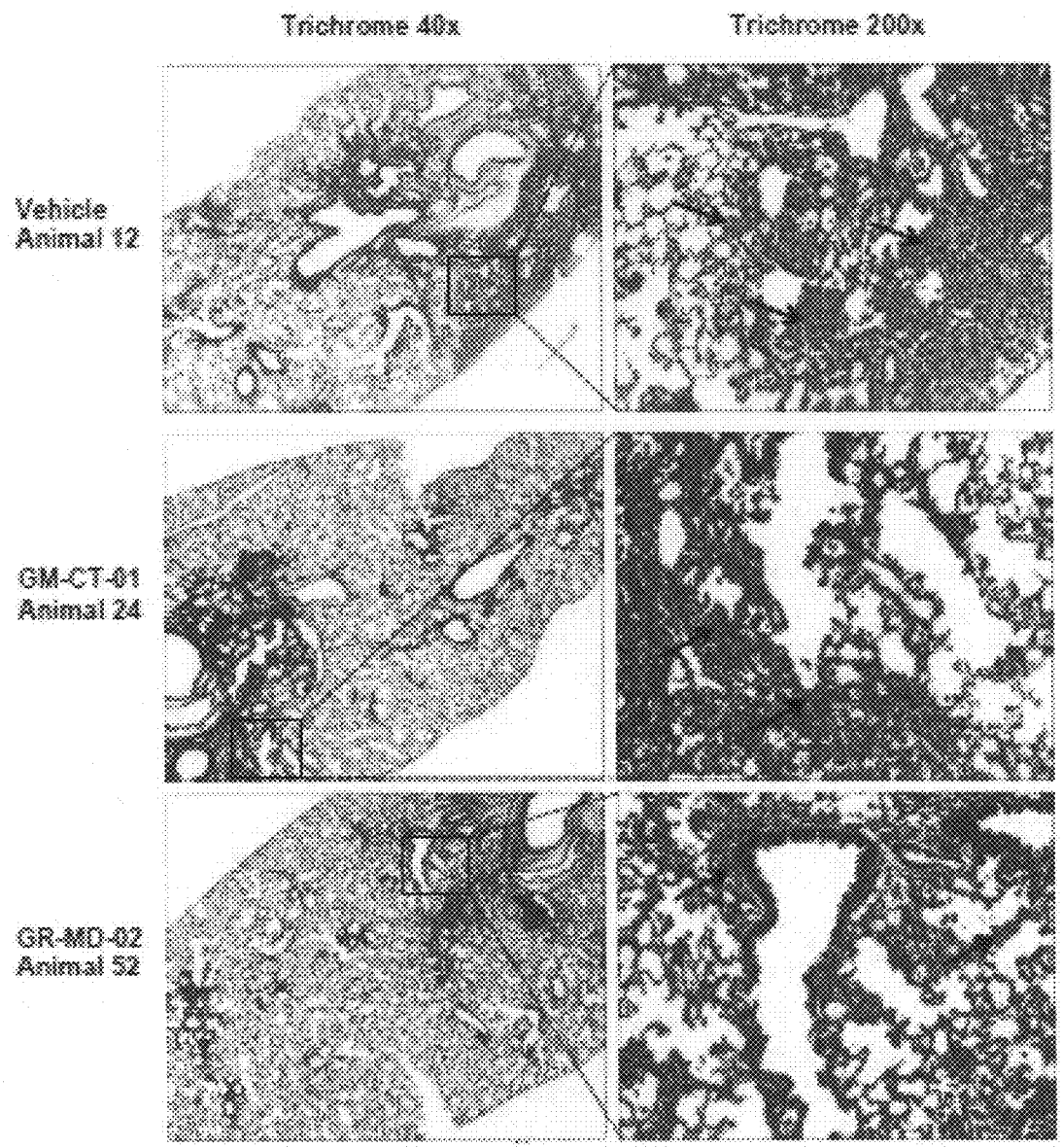
FIG. 14 are representative photomicrographs with trichrome from treated and control groups, according to one embodiment of the invention.

Lung pathology with trichrome stain of saline control, vehicle+bleomycin, GM-CT-01 and GR-MD-02 treated animals was examined. All tissue samples were examined and examples are shown in FIG. 14. GR-MD-02 treatment was found to be effective at reducing fibrosis, while GM-CT-01 had less effect. Vehicle-treated animals tended to have contiguous areas of fibrosis affecting large areas of most lung lobes. GR-MD-02 treated animals had smaller areas of fibrosis. There were often small knot-like formations or small masses of fibrosis, but these tended not to aggregate to the large formation seen in the vehicle-treated animals and to affect a smaller percentage of lungs.

Figure 15:
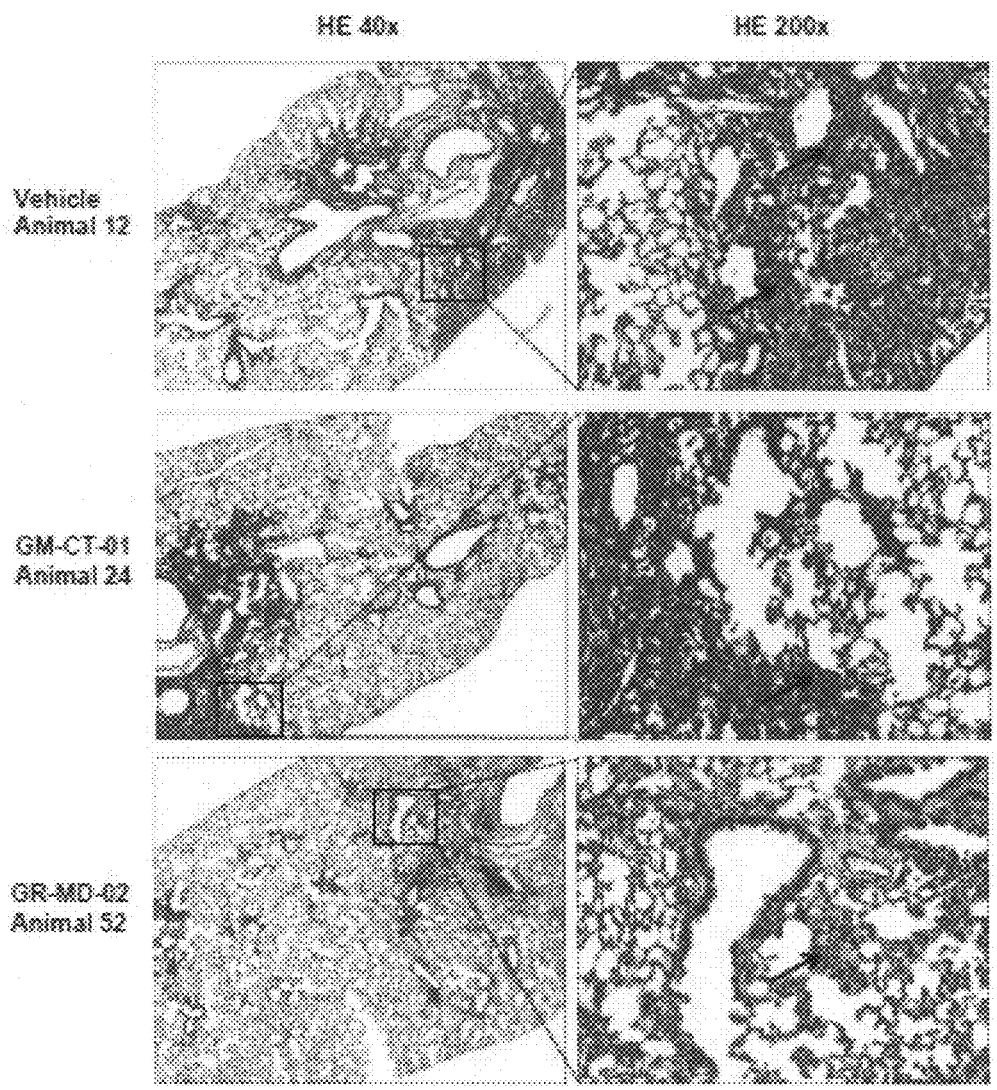
FIG. 15 are representative photomicrographs with H & E from treated and control groups, according to one embodiment of the invention.

Representative images with H & E are shown in FIGS. 15. H & E images show the same basic features as those stained with the trichrome stain. The vehicle control animals showed areas of dense fibrosis. There was some reduction in the fibrosis in the GM-CT-01 treated animals as indicated by more air space in the regions of fibrosis. In the GR-MD-02 treated animals there was a marked decrease in fibrous tissue.

Under the conditions of this study, both GM-CT-01 and GR-MD-02 treatment were effective at reducing pulmonary fibrosis in the bleomycin induced pulmonary fibrosis mouse model.

The results showed that GR-MD-02 exhibited the strongest anifibrotic effect under the conditions used. Animals in this group tended to have reduced percent of fibrotic lung, inflammation, semi quantitative general fibrosis score and fibrosis index score. While these changes were not statistically significant, they were noticeable and there were clear trends in the data supportive of a positive treatment effect.

The results showed that GM-CT-01 exhibited a more modest positive treatment effect. The percent of lung affected and semiquantitative fibrosis score were notably reduced but these findings were not statistically significant. There was less improvement in the index and inflammation scores. Regardless, there were clear trends in the data supportive of a positive treatment effect.

Conclusions

In the early treatment model, both GR-MD-02 and GM-CT-01 were shown to markedly reduce lung weight and hydroxyproline content, with reduction of histological evidence of inflammation and fibrosis when compared to vehicle-treated bleomycin mouse model.

Treatment: results showed that GR-MD-02 was more effective than GM-CT-01 in treating pulmonary fibrosis in the mouse model.

A mouse chronic model, such as intravenous bleomycin, can be used in future studies to evaluate the effect of different dosages and/or different schedules of administration.

While this invention has been particularly shown and described with references to preferred embodiments thereof, it will be understood by those skilled in the art that various changes in form and details may be made therein without departing from the scope of the invention. All publications, patents and sequence database entries mentioned herein are hereby incorporated by reference in their entirety as if each individual publication or patent was specifically and individually indicated to be incorporated by reference.

The invention claimed is:

1. A method comprising:
   a. obtaining a composition for parenteral or enteral administration comprising a galacto-rhamnogalacturonate in a pharmaceutical acceptable carrier, wherein the galacto-rhamnogalacturonate comprises a 1,4-linked galacturonic acid (GalA) and methyl galacturonate (MeGalA) residues backbone linked to branched heteropolymers of alternating oliqomers of α-1,2 linked rhamnose and α-1,4-linked GalA residues, the rhamnose residues carrying a primary branching of oligomers of 1,4-β-D-galactose residues, 1,5-α-L-arabinose residues, or combinations thereof, and wherein the 1,4-β-D-galactose and 1,5-α-L-arabinose residues are present in a 2:1 to a 3:1 ratio, and
   b. administering to a subject in need thereof an effective dose of the composition, that results in at least one of the following:
   at least 5% reduction of lung edema,
   at least 5% reduction of lung pathology severity scores associated with lung fibrosis,
   at least 5% reduction of lung tissue hydroxyproline accumulation,
   at least 5% reduction of expression of pro-inflammatory proteins,
   at least 5% reduction of expression of fibrogenic proteins,
      wherein the subject in need thereof has at least one of the following: a primary or secondary lung fibrotic disease.

2. The method of claim 1 wherein the effective dose is equivalent to an animal dose of 10 mg/kg to 180 mg/kg given once, twice or three times weekly.

3. The method of claim 1 wherein the pro-inflammatory proteins comprise TGF-beta, IL-6, IL-8, IL-13, osteopontin, TNF-alpha, CXCL-9/10, or VEGF.

4. The method of claim 1 wherein the fibrogenic proteins comprise collagen, or elastin.

5. The method of claim 1 wherein the galacto-rhamnogalacturonate further comprises xylose, glucose, fucose residues or combination thereof.

6. The method of claim 1 wherein the galacto-rhamnogalacturonate is substantially free of 1,5-α-L-Ara residues.

7. The method of claim 1 wherein the 1,4-β-D-galactose residues, the 1,5-α-L-arabinose residues or combination thereof represent at least 10 molar percent of the total molar carbohydrates.

8. The method of claim 1 wherein the galacto-rhamnogalacturonate has an average molecular weight ranging from 5 kDa to 55 kDa as determined by SEC-RI and/or the SEC-MALLS methods.

9. The method of claim 1 wherein the galacto-rhamnogalacturonate has an average molecular weight ranging from 2 kDa to 80 kDa as determined by SEC-RI and/or the SEC-MALLS methods.

10. The method of claim 1 wherein the galacto-rhamnogalacturonate has an average molecular weight ranging from 20 kDa to 70 kDa as determined by SEC-RI and/or the SEC-MALLS methods.

* * * * *